United States Patent [19]

Tanaka et al.

[11] Patent Number: 4,900,815

[45] Date of Patent: Feb. 13, 1990

[54] SULFATED POLYSACCHARIDE DS4152

[75] Inventors: Noriko Tanaka; Kazuhiro Inoue; Hiroshi Korenaga; Hidemasa Ogawa, all of Tokyo, Japan

[73] Assignee: Daiichi Seiyaku Co., Ltd., Tokyo, Japan

[21] Appl. No.: 51,754

[22] Filed: May 20, 1987

[30] Foreign Application Priority Data

May 23, 1986 [JP] Japan .................. 61-118847
Feb. 5, 1987 [JP] Japan .................. 62-25437

[51] Int. Cl.$^4$ .................. C08B 37/00; A61K 31/715; A61K 31/735

[52] U.S. Cl. .................. 536/54; 514/54; 424/116; 424/117

[58] Field of Search .................. 514/54; 536/54; 424/116, 117

[56] References Cited

FOREIGN PATENT DOCUMENTS 114589 12/1983 European Pat. Off. .
56-67301 6/1981 Japan .
57-42627 10/1982 Japan .
59-25329 9/1984 Japan .

Primary Examiner—Ronald W. Griffin
Attorney, Agent, or Firm—Oblon, Spivak, McClelland, Maier & Neustadt

[57] ABSTRACT

A sulfated polysaccharide DS4152 useful as an angiogenesis inhibitor or antitumor agent is provided selectively. As the sodium salt, it has the following physicochemical characteristics. Molecular weight by the gel filtration method: 29,000±3,000. Elemental analysis: C: 24.42–25.76%, H: 3.34–3.98%, N: 0.51–0.89%, S: 10.6–11.7% and P: 0.77–1.06%. Sugar and protein contents: Sugar content (%): 57±3 (by phenol sulfuric acid method; standard: galactose). Protein content (%): 1±0.5 (by the Lowry-Folin's method; standard: bovine serum albumin). Specific rotatory power $[\alpha]_D^{25}$: $-37°±1°$ (0.5% aq. solution). Characteristic absorption bands in infrared absorption spectrum: 1240, 840 (shoulder), 810 (cm$^{-1}$; KBr).

14 Claims, 2 Drawing Sheets

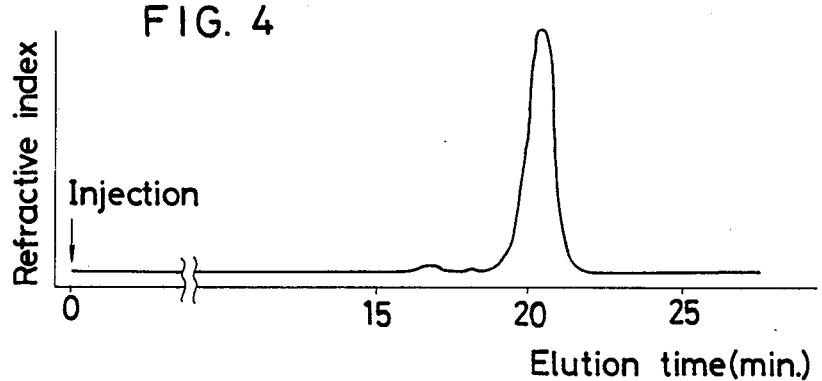

SULFATED POLYSACCHARIDE DS4152

BACKGROUND OF THE INVENTION

1. Field of the Invention

This invention relates to a novel sulfated polysaccharide DS4152 and an angiogenesis inhibitor comprising DS4152 as an active ingredient as well as an angiogenesis inhibitor comprising DS4152 and a steroid or antiestrogen as a further active ingredient.

2. Description of the Prior Art

A fermentation product of Micrococcus sp.AT-25 (now corrected to Arthrobacter sp.AT-25) has already been known to contain a sulfated polysaccharide DF4639 which has fibrinolysis-inductive effects, protective effects against infection and interferon-inductive effects (Japanese Pat. Laid-Open Nos. 67301/1981, 42627/1982 and 25329/1984).

SUMMARY OF THE INVENTION

With a view toward determining biological characteristics of the sulfated polysaccharide DF4639 which were expected to have various utility, the present inventors conducted an investigation thereon. As a result, it was found that DF4639 has a strong pyrogenic activity. A further investigation has then been carried out to get rid of its pyrogenic effects. As a result, it has now been found that DF4639 is a mixture of several ingredients and one of its ingredients, named DS4152, does not have pyrogenic effects and moreover has superior antiangiogenic activity effects compared with DF4639.

In addition, the present inventors have also found that the antiangiogenic inhibitory effects are enhanced synergistically when this DS4152 is combined with a steroid or antiestrogen.

The present invention has been completed on the basis of the above-described findings. An object of this invention is therefore to provide the novel sulfated polysaccharide DS4152.

Another object of this invention is to provide an angiogenesis inhibitor which comprises the sulfated polysaccharide DS4152 as an active ingredient.

A further object of this invention is to provide an angiogenesis inhibitor which comprises, as active ingredients, the sulfated polysaccharide DS4152 and a steroid or antiestrogen.

In one aspect of this invention, there is thus provided a sulfated polysaccharide DS4152 having, as the sodium salt thereof, the following physicochemical characteristics:

(1) Molecular weight (by the gel filtration method): 29,000±3,000
(2) Elemental analysis:
   C:24.42–25.76%
   H:3.34–3.98%
   N:0.51–0.89%
   S:10.6–11.7%
   P:0.77–1.06%
(3) Sugar and protein contents:
   Sugar content (%): 57±3 (by phenolsulfuric acid method; standard: galactose)
   Protein content (%): 1±0.5 (by the Lowry-Folin's method; standard; bovine serum albumin)
(4) Specific rotatory power:
   $[\alpha]_D^{25}$: $-37° \pm 1°$ (0.5% aq. solution)
(5) Characteristic absorption bands in infrared absorption spectrum:
   1240, 840 (shoulder), 810 (cm$^{-1}$; KBr)
(6) Solubility:
   Freely soluble in water but practically insoluble in organic solvents such as ether, benzene, chloroform, methanol and ethanol.
(7) Color reaction:
   Positive in the phenol-sulfuric acid reaction, anthrone-sulfuric acid reaction, biuret reaction and Lowry-Folin's reaction. In the form of an acid hydrolyzate, also positive in the Elson-Morgan's reaction and ninhydrin reaction. Negative in the carbazole reaction and Sakaguchi reaction.
(8) Distinction of acidic, neutral or basic:
   pH 6–8 (3% aq. solution)
(9) Contents of constituent sugar, sulfate groups and phosphorus:
   The molar ratio of D-glucose: D-galactose:SO$_3$Na:P(phosphorus) is approximately 10:61:73:6.
(10) Constituent amino acids and amino sugars:
   An analysis of an acid hydrolysate by an amino acid analyzer indicates the existence of alanine, glycine, glutamic acid, diaminopimelic acid, glucosamine and muramic acid.

In another aspect of this invention, there is also provided an angiogenesis inhibitor comprising a sulfated polysaccharide DS4152 as an active ingredient.

In a further aspect of this invention, there is also provided an antitumor agent comprising a sulfated polysaccharide DS4152 as an active ingredient.

In a still further aspect of this invention, there is also provided an angiogenesis inhibitor comprising, as active ingredients, a sulfated polysaccharide DS4152 and a steroid or antiestrogen.

In a still further aspect of this invention, there is also provided an antitumor agent comprising, as active ingredients, a sulfated polysaccharide DS4152 and a steroid or antiestrogen.

Although DS4152 of this invention itself has strong antiangiogenic effects, superior antiangiogenic effects can be exhibited when employed in combination with a steroid or antiestrogen. For example, an antiestrogen is used as an endocrinotherapeutic for breast cancer as described above. It is however accompanied by a drawback that its application is limited to hormone-dependent breast cancer having a estrogen receptor. It is well known that a breast cancer is a hormone-dependent cancer, though their hormone dependency is heterogenous even in the same tumor and further alters and disappears during the therapy. The combined use of an antiestrogen and DS4152 however develops strong antiangiogenic activity so that the anti-tumor effects of the antiestrogen are enhanced against hormone-dependent tumors and are also produced against hormone-independent solid tumors.

DS4152 itself is useful as an angiogenesis inhibitor. When DS4152 is however combined further with a steroid or antiestrogen, their effects are enhanced synergistically so that the combined use of these active ingredients is useful especially, for example, as an angiogenesis inhibitor capable of inhibiting the development of new vessels in a tumor and preventing the growth of the cancer.

BRIEF DESCRIPTION OF THE/DRAWINGS

The above and other objects, features and advantages of the present invention will become apparent from the following description and the appended claims, taken in conjunction with the accompanying drawings, in which:

FIGS. 1, 2 and 3 are high-performance gel filtration chromatograms of DS4152 obtained in Example 1(A), DF4639 and H fraction, respectively, each of which was measured under the following conditions:
  column:(7.5×600 mm) of G3000 SW
  carrier:0.1 M AcOK buffer (pH 6.5)
  flow rate:0.9 m;/min
  temperature:40° C.
  chart speed:1.0 cm/min; and FIG. 4 is a high-performance gel filtration chromatogram of DS4152, which had been obtained in Example 1(B), measured under the following conditions:
  column:the same column as that used in the measurement of the chromatogram of FIG. 3.
  carrier:0.1 M AcONa buffer (pH 6.5)
  flow rate:0.8 ml/min
  temperature:40° C.
  chart speed:1.0 cm/min.

DETAILED DESCRIPTION OF THE INVENTION AND PREFERRED EMBODIMENTS

Figure 1:
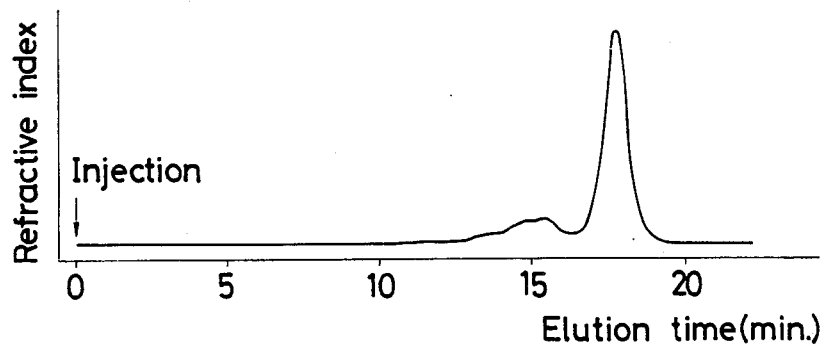

The term "angiogenesis inhibitor" as used herein means an agent capable of suppressing the formation of new blood vessels which is not only extremely important for the growth of the embryo, luteinization, the healing of wounds and the like but also deeply related to several pathological conditions such as chronic inflammation including rheumatoid arthritis, immune response etc., and tumor growth, etc. The angiogenesis inhibitor is therefore useful for the treatment and prevention of various diseases of which development may be related to angiogenesis for example, rheumatoid arthritis, proliferating retinitis, psoriasis, diabetic retinitis, retrolental fibroplasia and so on. It is said that a tumor, in particular, induces strong vascularization and the blood supplied through the newly-developed vessels accelerates further tumor growth. Accordingly, the vascularization inhibitor is also useful as an anti-tumor agent.

The sulfated polysaccharide DS4152 of this invention can be obtained by removing pyrogenic substances having molecular weights of $15 \times 10^4$ or more by a suitable molecular weight fractionating method, for example, the gel filtration method, ultrafiltration method or alcohol precipitation method from DF4639 (see, Japanese Pat. Laid-Open No. 67301/1981) which is purified from a culture broth of Arthrobacter sp.AT-25 (FERM BP-1357), which has been deposited in the name of "Micrococcus sp.AT-25" under FERM P-5255 with the Fermentation Research Institute, Agency of Industrial Science and Technology, Ministry of International Trade and Industry, the Japanese Government.

According to the gel filtration method by way of example, DF4639 is subjected to gel filtration by using a suitable carrier for gel filtration, for example, Sephacryl S-300 (trade name, product of Pharmacia AB, Uppsala, Sweden). The resulting fractions are then subjected to a high-performance gel filtration chromatography on a "G3000 SW Column" (trade name, product of Toyo Soda Mfg. Co., Ltd., Shinnanyo, Yamaguchi, Japan). Fractions (H Fraction) showing peaks in the void volume and fractions (L Fraction) giving no peaks in the void volume and eluted in a molecular weight range of about $2 \times 10^4$–$8 \times 10^4$ are separately collected and dialyzed against deionized water.

The thus-obtained inner dialyzates are separately concentrated, followed by filtration. The filtrates were separately poured with stirring into several volumes of ethanol and the resulting precipitates were separately collected. After washing the precipitate successively with 90% ethanol, ethanol and acetone, the precipitates were separately dried under reduced pressure to obtain the intended DS4152 (L Fraction) and pyrogenic substances (H Fraction).

On the other hand, the ultrafiltration can be effected by using a suitable membrane (e.g., "YM10", "YM30", "XM50" or "PM30", trade names, products of Amicon Corporation; or "NOVA 100", "OMEGA 100", "NOVA 50" or "OMEGA 50", trade names, products of Filtron Technology Corporation; or the like; typically, "YM10"), applying a pressure (0.5–5 kg/cm² or so) with nitrogen gas or by a pump and then collecting the filtrate as DS4152. The suitable solvent may be water-ethanol (10:2-3) or water. The ultrafiltration is conducted usually at 4° C.—room temperature.

DS4152 obtained in the above manner has, as the sodium salt thereof, the following physicochemical characteristics:

(1) Molecular weight (by the gel filtration method):
  29,000±3,000

(2) Elemental analysis, is (ranges of 5 lots):
  C:24.42–25.76%
  H 3.34–3.98%
  N:0.51–0.89%
  S:10.6–11.7%
  P:0.77–1.06%

(3) Sugar and protein contents:
  Sugar content (%): 57±3 (by the phenol-sulfuric acid method; standard: galactose)
  Protein content (%): 1±0.5 (by the Lowry-Folin's method; standard: bovine serum albumin)

(4) Specific rotatory power:
  $[\alpha]_D^{25}$: $-37° \pm 1°$(0.5% aq. solution)

(5) Characteristic absorption bands in infrared absorption spectrum:
  1240, 840 (shoulder), 810 (cm$^{-1}$ KBr)

(6) Solubility:
  Freely soluble in water but practically insoluble in organic solvents such as ether, benzene, chloroform, methanol and ethanol.

(7) Color reaction:
  Positive in the phenol-sulfuric acid reaction, anthrone-sulfuric acid reaction, biuret reaction and Lowry-Folin's reaction. In the form of an acid hydrolyzate, also positive in the Elson-Morgan's reaction and ninhydrin reaction. Negative in the carbazole reaction and Sakaguchi reaction.

(8) Distinction of acidic, neutral or basic:
  pH 6–8 (3% aq. solution)

(9) Contents of constituent sugar, sulfate groups and phosphorus:
  The molar ratio of D-glucose: D-galactose:SO₃.Na:P(phosphorus) is approximately 10:61:73:6.

(10) Constituent amino acids and amino sugars:
  An analysis of an acid hydrolysate by an amino acid analyzer indicates the existence of alanine, glycine, glutamic acid, diaminopimelic acid, glucosamine and muramic acid.

Although the above-described DS4152 itself has antiangiogenic activity effects as will be demonstrated in Examples to be given subsequently, still better antiangiogenic activity effects are exhibited when combined with a steroid or antiestrogen.

In the angiogenesis inhibitor of this invention, heparin, low-molecular weight heparin or the like may also be used in lieu of DS4152.

Steroid hormones such as prednisolone, 6α-methylprednisolone and dexamethasone have already been reported to be effective for the suppression of vascularization induced experimentally in the chorioallantoic membrane (CAM) of chick embryo, rabbit cornea and hamster cheek pouches [Cancer Res., 39, 1305 (1979); J. Natl. Cancer Inst., 57, 769 (1976); and Proc. Natl. Acad. Sci. USA, 78, 1176 (1981)]. Among steroid hormones, glucocorticoids (prednisolone, prednisone, betamethasone, etc.) are used for the treatment of leukemia, malignant lymphoma, breast cancer and prostatic cancer.

Further, testosterone propionate and fluoxymesterone and the like which are androgens of the androstane nucleus type are employed as anti-breast cancer agents. They have been reported to give 20-30% effectivity [Oncologia, 10, 72 (1984)].

In addition, certain progesterone derivatives, testosterone derivatives and estrogens are used for the treatment of prostatic cancer.

Illustrative examples of steroids usable in combination with DS4152 may include the followings. (1) Steroid hormones containing the pregnane nucleus, namely, glucocorticoids:

Cortisone and its derivatives (acetate, enanthate, undecylate, etc.); hydrocortisone and its derivatives (acetate, hemisuccinate, caproate, etc.); prednisone and its derivatives; prednisolone and its derivatives (acetate, hemisuccinate, phosphate, butylacetate, tetrahydrophthalate, trimethylacetate, etc.); methylprednisolone and its derivatives (acetate, hemisuccinate, etc.); and betamethasone and its derivatives (phosphate, valerate, etc.).

Some glucocorticoid isomers in which the 11hydroxyl group has the α-configuration, for example, 11α-epihydrocortisone; and tetrahydrometabolites of the above-mentioned glucocorticoids, irrespective of glucocorticoid activity.

Corpus luteum hormones progesterone and hydroxyprogesterone, and their derivatives (acetates, etc.); dydrogestrone and its 17α-acetoxy derivative (Duphaston, trade name); etc. Mineralocorticoids: aldosterone and desoxycorticosterone, and their derivatives (acetates, trimethylacetates, enanthates, phenylpropionates, etc.).

(2) Steroid hormones containing the androstane nucleus, namely, androgens:

Androsterone and testosterone, and their derivatives (propionates, enanthates, butyrates, caprylate etc.).

Epithiostanol and mepitiostanon, and their derivatives.

Fluoxymesterone and its derivatives; methyltestosterone and its derivatives; and stanolone and its derivatives.

(3) Steroid hormones containing the estrane nucleus, namely, follicle hormones:

Estrone and its derivatives; estradiol and its derivatives (benzoate, dipropionate, valerate, undecenoate, etc.); estriol and its derivatives (tripropionate, etc.).

As exemplary antiestrogens on the other hand, may be mentioned clomiphene, nafoxidine, tamoxifen, 4-hydroxytamoxifen and N-desmethyltamoxifen, and physiologically-acceptable salts thereof, e.g., their organic acid salts such as citrate, their inorganic acid salts such as hydrochloride, etc.

Owing to their little side effects, these antiestrogens are widely used as long-term endocrinotherapeutic agents for breast cancer, especially, recurrent and advanced breast cancer.

As preparation forms of the angiogenesis inhibitor of this invention, may be mentioned various preparation forms containing the active ingredient along with medicinally-acceptable carriers and excipients, for example, solutions of the active ingredient dissolved water or various transfusion solutions, powders, granules, tablets, injections, suppositories.

When the angiogenesis inhibitor of this invention contains DS4152 in combination with a steroid or antiestrogen, the active ingredients may be separately formulated into single-ingredient preparations of one of the above-described forms and then provided as combined preparations, or may be formulated together into a two-ingredient preparation.

The angiogenesis inhibitor of this invention may be administered intravenously, intra-arterially, orally, subcutaneously, intrarectally, mucosally or directly into tumor masses. Its dose may be 1-2,000 mg in terms of DS4152 as a daily oral dose for an adult. A steroid may suitably be administered at a dose of 10-1,000 mg, usually, 30-60 mg in the case of an androgen or glucocorticoid. It may be preferable to reduce the dose gradually. For a progesterone, the suitable daily dose may be 100-1,200 mg. In the case of an antiestrogen, the daily dose may be suitably 5-100 mg, usually, 20-40 mg. When the angiogenesis inhibitor is administered by injection, the appropriate dose may usually be about one fifth the oral dose.

The above administration method and dose may be followed substantially when the angiogenesis inhibitor of this invention is used as an anti-tumor agent.

Having generally described the invention, a more complete understanding can be obtained by reference to certain specific examples, which are provided herein for purposes of illustration only and are not intended to be limiting unless otherwise specified.

EXAMPLES

This invention will hereinafter be described further by the followings Examples and Referential Examples.

REFERENTIAL EXAMPLE 1

One loopful of cells of Arthrobacter sp. AT-25 on a slant of agar medium were inoculated to a 500-ml shaking flask containing 100 ml of a liquid culture medium which was composed of 2% of glucose, 0.5% of peptone, 0.5% of corn steep liquor, 0.3% of yeast extract, 0.5% of sodium chloride and 0.3% of calcium carbonate. The cells were cultured at 30° C. with shaking for 3 days to obtain a seed culture broth. Then, 20 l of a culture medium composed of 2% of glycerin, 0.5% of ammonium sulfate, 0.1% of potassium dihydrogen phosphate, 0.05% of sodium sulfate and 0.2% of yeast extract was added to a 30-l jar fermentor. After sterilizing the culture medium at 120° C. for 20 minutes, its pH was adjusted to 7.5. Six hundred milliliters of the seed culture broth were inoculated into the thus-prepared culture medium and then cultured for 159 hours under the following conditions: temperature: 30° C., aeration: 10 l/min., and agitation: 250 rpm. The resultant culture broth was centrifuged to remove the cells. After adding 500 ml of a 10% aqueous solution of cetylpyridinium chloride to 18 l of the resulting supernatant and allowing the thus-obtained mixture to stand for 24 hours, the resulting precipitate was collected by centrifugation. The precipitate was then added to 600 ml of a 3 M sodium chloride-10%(v/v)ethanol solution and the resultant mixture was stirred thoroughly to dissolve the precipitate. Thereafter, 1.6 l of ethanol was added and the resultant precipitate was collected by filtration with a glass filter The precipitate was washed first with ethanol and then with acetone and was then dried to obtain 37.0 g of crude powder. The crude powder was dissolved in 500 ml of water and the pH of the resulting solution was adjusted to about 1.0 with 1 N hydrochloric acid. The resultant precipitate was removed by centrifugation. The supernatant was neutralized, followed by an addition of 500 ml of a 10% aqueous solution of cetyltrimethylammonium bromide. The thus-formed precipitate was collected by centrifugation. After washing the precipitate thoroughly with 1 M sodium chloride, 150 ml of a 3 M sodium chloride-10%v/v)ethanol solution was added and the resultant mixture was stirred thoroughly to dissolve the precipitate. After an addition of 450 ml of ethanol, the mixture was allowed to stand overnight and the resulting precipitate was collected by centrifugation. After washing the precipitate with ethanol, it was dissolved again in 150 ml of water. The solution was filtered through a glass filter and a small amount of the precipitate on the filter was washed with 50 ml of water. The filtrate and washing were combined and poured with stirring into 2 l of ethanol, thereby forming a white precipitate. The precipitate was collected on a glass filter by filtration and was washed successively with ethanol, acetone and ethyl ether. It was then dried at 55° C. for 5 hours under reduced pressure to obtain 13.9 g of DF4639 as white powder.

EXAMPLE 1(A)

DF4639 (5.0 g) obtained in accordance with the method described in Japanese Pat. Laid-Open No. 67301/1981 was dissolved in 15 ml of a 0.1 M aq. NaCl solution. The resulting solution was subjected to chromatography on a column (5.0×80 cm) of Sephacryl S-300 (trade name, product of Pharmacia AB) equilibrated with a 0.1 M aq. NaCl solution. The column was eluted with the same solvent and 18 ml-fractions were collected. The thus-obtained fractions were separately subjected to high-performance gel filtration chromatography on a "G3000 SW Column" (trade name, product of Toyo Soda Mfg., Co., Ltd.; eluent: 0.1 M potassium acetate buffer, pH 6.5). Collected were the fractions each of which did not give any peak in the void volume and was eluted within a molecular weight range of about $2 \times 10^4 - 8 \times 10^4$ (standard: dextran). Those fractions were dialyzed against diionized water. The inner dialyzate was concentrated to about 50 ml, followed by filtration. The filtrate was added dropwise with stirring into about 400 ml of ethanol and the resulting precipitate was collected. After washing the precipitate successively with 90% ethanol, ethanol and acetone in order, it was dried at 50° C. for 6 hours under reduced pressure to obtain 3.8 g of the intended product, namely, DS4152 as white powder.

On the other hand, the fractions each of which gave a peak in the void volume in the above-described high-performance gel filtration chromatography were also collected (about 90 ml) and treated in the same manner as the above-mentioned DS4152, thereby obtaining 0.18 g of H Fraction as pale yellow powder.

Physicochemical and biological characteristics of DS4152 will next be shown in comparison with those of H Fraction.

(a) Sugar, Protein, S and P Contents (Table 1)

TABLE 1

|  | Sugar (%)[1] | S (%)[2] | Protein (%)[3] | P (%)[4] |
| --- | --- | --- | --- | --- |
| DS4152 | 56 | 11.1 | 1.1 | 0.88 |
| DF4639 | 54 | 10.8 | 1.3 | 0.86 |
| H Fraction | 42 | 7.9 | 7.6 | 0.72 |

[1]Phenol-sulfuric acid method (standard: galactose).
[2]Antonopoulos's method [C.A. Antonopoulos, Acta Chem. Scand., 16, 1521 (1962)].
[3]Lowry-Folin's method (standard: bovine serum albumin).
[4]Chen et al's method [P.S. Chen, et al., Anal. Chem. 28, 1756 (1956)].

(b) Molar Ratio of Constituent Galactose, Glucose, Sulfate Groups and Phosphorus A sample was hydrolyzed at 100° C. for 5 hours in 1 N sulfuric acid and then subjected to a desalting treatment with an ion-exchange resin. Sugars were thereafter converted into alditol acetates by a method known per se in the art and then analyzed by a gas chromatography. On the other hand, the molar ratio of sulfate groups and phosphorus was calculated from S and P contents (%).

TABLE 2

|  | Galactose | Glucose | Sulfate groups | P |
| --- | --- | --- | --- | --- |
| DS4152 | 6.1 | 1.0 | 7.3 | 0.6 |
| DF4639 | 6.2 | 1.0 | 7.3 | 0.6 |
| H Fraction | 6.2 | 1.0 | 6.9 | 0.6 |

Table 2 shows typical molar ratios of the individual components.

(c) Identification of Constituent Amino Acids and Amino Sugars

After subjecting DS4152 to hydrolysis at 100° C. for 16 hours in 3 N hydrochloric acid, the resultant hydrolyzate was analyzed by an amino acid analyzer by a method known per se in the art. As a result, there were observed peaks corresponding to alanine, glycine, glutamic acid, diaminopimelic acid, glucosamine and muramic acid.

(d) Specific Rotatory Power: $[\alpha]_D^{25}(c=0.5, \text{water})$

TABLE 3

| Specific rotatory power | |
| --- | --- |
| DS4152 | −37° |
| DF4639 | −36° |
| H Fraction | −34° |

(e) Elution Profile of Gel Filtration

Figure 2:
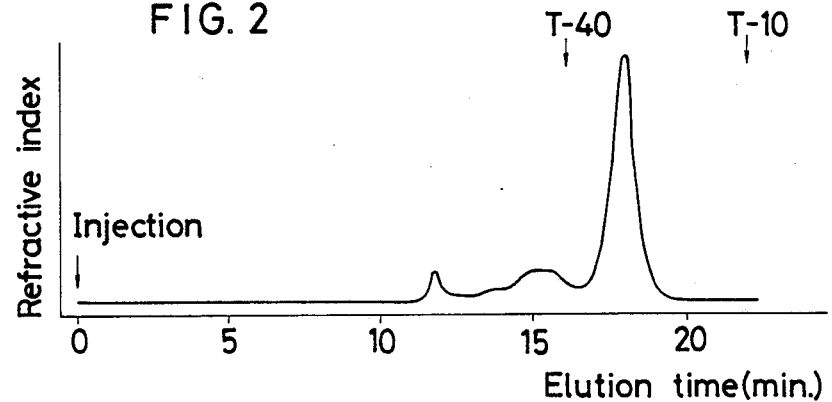
Figure 3:
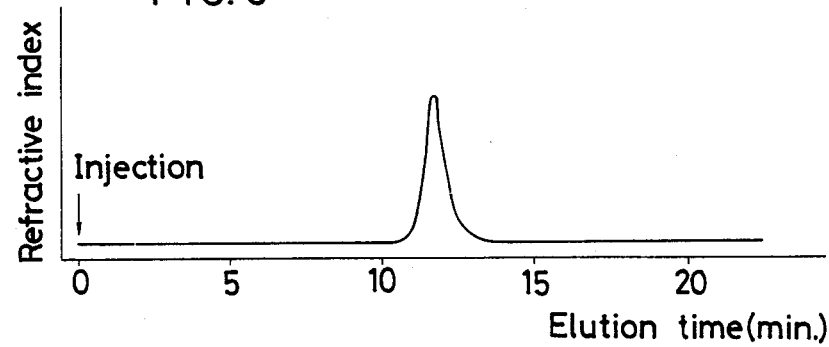

FIGS. 1, 2 and 3 show respectively high performance gel filtration chromatograms of DS4152 obtained in Example 1(A), DF4639 and H Fraction ["G3000 SW Column" (trade name, product of Toyo Soda Mfg. Co., Ltd.) was used. Standard materials: dextran T-10 and T-40]. FIG. 4 is a high-performance gel filtration chromatogram of DS4152 obtained in Example 1(B).

(f) Ultraviolet Absorption Spectrum

No maximum absorption was observed at 220–340 nm when measured in the form of a 2 mg/ml aq. solution.

(g) Infrared Absorption Spectrum (KBr Tablet)

Absorption characteristic of sulfated polysaccharides appeared at 1240, 840 (shoulder) and 810 cm$^1$.

(h) Structural Feature

DS4152 is suggested to have the molecular structure of a sulfated polysaccharide in which peptidoglycan moieties are linked via muramic acid phosphate to sugar moieties formed principally of D-galactose and D-glucose.

(i) Pyrogen Test

Results of a pyrogen test conducted following the Japanese Pharmacopoeia (10th edition) are shown in Table 4.

TABLE 4

| Sample | Dose μg/ 10 ml /kg | Degree of fervescence, °C. Individual rabbits | | | Total | Judge-* ment |
|---|---|---|---|---|---|---|
| DS4152 | 75 | 0.20 | 0.10 | 0.15 | 0.45 | — |
| | 375 | 0.20 | 0.50 | 0.20 | 0.90 | — |
| DF4639 | 15 | 1.55 | 1.25 | 1.40 | 4.20 | + |
| | 75 | 1.40 | 2.00 | 1.80 | 5.20 | + |
| H Fraction | 15 | 1.90 | 1.40 | 2.20 | 5.50 | + |
| | 75 | 1.80 | 1.75 | 2.65 | 6.20 | + |

*+: Positive, —: Negative (j) Acute Toxicity of DS4152 (Mouse, Intravenous Injection)

LD$_{50}$:above 2,000 mg/kg.

EXAMPLE 1(B)

DF4639(6.0 g) obtained in Referential Example 1 was dissolved in 300 ml of a 10:3 mixed solvent of water and ethanol, and the resultant solution was subjected to ultrafiltration at room temperature through a "YM10" membrane (41.8 cm$^2$, product of Amicon Corporation) while pressurizing the solution under 1.5 kg/cm$^2$ with nitrogen gas. While adding a fresh supply of the above solvent, the ultrafiltration was continued until the volume of the filtrate reached about 3 l. The filtrate was the concentrated to about 50 ml. After adding and dissolving 100 mg of sodium acetate in the thus-concentrated filtrate, the resultant solution was centrifuged. The supernatant was then added dropwise into about 500 ml of ethanol. The resulting precipitate was collected, washed successively with 90% ethanol, ethanol and acetone, and then dried at 55° C. for 5 hours under reduced pressure, thereby obtaining 3.3 g of DS4152 as white powder. Thus obtained DS 4152 had the same properties as that obtained in Example 1(A) except for the followings:

Sugar contents:58%
Sulfur contents:11.3%
Protein contents:0.9%
P:0.92%

EXAMPLE 2

CAM Angiogenesis Inhibition Test (Direct Method)

Using chick embryos, a test was carried out in accordance with the following method, which was a partial modification of the Taylor-Folkman's method Nature, 297, 307 (1982)].

Either DS4152 or heparin dissolved in physiological saline was added to the CAM of each 4–5 day old fertilized chicken 1 egg (species: NORIN CROSS) and then the eggs were incubated at 37° C.

Two days after the addition of the agent, the degree of the CAM vascularization was compared with that of a control to which physiological saline was only added. The 50% vascularization inhibition dose (ID$_{50}$) was calculated by the probit method.

As a result, the ID$_{50}$ value of DS4152 of this invention was found to be 160 ng. In contrast, heparin showed no effect even at 100 μg.

EXAMPLE 3

CAM Angiogenesis Inhibition Test (Direct Method)

In the same manner as in Example 2, combination effects of a steroid and DS4152 were examined. As the steroid, cortisone acetate was used at a dose of 0.5 μg per embryo (i.e., at a dose not to give any influence to the vascularization). The activities of DF4639 and H Fraction were also investigated in the comparison with that of DS4152. Results are summarized in Table 5.

TABLE 5

| | DS4152 | DF4639 | H Fraction |
|---|---|---|---|
| ID$_{50}$ (ng/chick embryo) | 3 | 30 | 600 |

EXAMPLE 4

In a manner similar to that employed in Example 2, ID$_{50}$ value of the combinations use of various steroids and DS4152 were determined. As a result, the inhibitory activities of the various steroids against angiogenesis of the chick CAM showed 2.1–100 fold increase in the presence of 10 ng of DS4152. (Table 6).

TABLE 6

| | ID$_{50}$ (μg/embryo) | | |
|---|---|---|---|
| Steroid | Alone | Used in combination with DS4152 (degree of increase, times) | |
| Cortisone acetate | 1.20 | 0.17 | (7.1) |
| Hydrocortisone | 1.10 | 0.16 | (6.9) |
| Prednisolone | 1.30 | 0.08 | (16.3) |
| 6α-Methyl-prednisolone | 1.15 | 0.03 | (38.3) |
| Betamethasone | 0.80 | 0.05 | (16.0) |
| Tetrahydro S | 1.00 | 0.01 | (100.0) |
| Progesterone | 1.02 | 0.49 | (2.1) |
| Medroxyprogesterone acetate | 1.12 | 0.42 | (2.7) |
| 17β-Estradiol | 1.96 | 0.28 | (7.0) |
| Fluoxymesterone | 1.24 | 0.12 | (10.3) |
| 5α-Androstane | 2.32 | 0.29 | (8.0) |

EXAMPLE 5

CAM Angiogenesis Inhibition Test (Direct Method)

A test was conducted in the same manner as in Example 2. Antiestrogens were separately dissolved or suspended in physiological saline and were added either alone or together with DS4152. The eggs with the agents were incubated at 37° C. Two days after the addition of the agents, the degrees of development of CAM vessels were individually compared with that of a control to which physiological saline was only added. (1) Table 7 shows the effects of antiestrogens on CAM angiogenesis in the presence of 0.01 μg of DS4152. The doses of each antiestrogen did not affect CAM vascularization. The angiogenesis was inhibited as much as 23.1–70.5%.

TABLE 7

| Antiestrogen | | DS4152 (μg) | |
|---|---|---|---|
| Agent | Amount added (μg) | 0 | 0.01 |
| Clomiphene citrate | 1 | −3.9 | 32.6 |
|  | 10 | −11.4 | 42.0 |
| Nafoxidine chloride | 1 | −4.3 | 23.1 |
|  | 10 | −3.2 | 31.6 |
| Tamoxifen citrate | 1 | −0.4 | 56.2 |
|  | 10 | 2.9 | 70.5 |

*Expressed in terms of percent inhibition based on the inhibition of the vascularization of the CAM of the control.

(2) Table 8 shows 50% angiogenesis inhibition doses of DS4152 and heparins when DS4152 and the heparins were separately used in combination with tamoxifen citrate in an amount of 1 μg which was too little to affect the vascularization.

TABLE 8

|  | DS4152 | low molecular weight heparin | heparin |
|---|---|---|---|
| 50% vascularization inhibition dose (μg) | 0.064 | 1.37 | 3.43 |

EXAMPLE 6

Antiangiogenic Effects (Ex Vivo)

DS4152 was dissolved in physiological saline and then administered subcutaneously or orally to male ICR mice. After 6 hours, the blood samples were collected and then prevented from coagulation with a 0.313% aqueous solution of sodium citrate. Each blood sample was added to the CAM of 5 day-old chick embryo in the same manner as in the direct method. The inhibitory effects were judged after two days. Results are summarized in Table 9.

TABLE 9

| Administration route | Dose (mg/kg) | Angiogenesis inhibition rate (%) |
|---|---|---|
| Oral | 3 | −5.9 |
|  | 30 | 26.4 |
|  | 300 | 62.7 |
| Subcutaneous | 3 | 1.6 |
|  | 30 | 37.8 |
|  | 300 | 66.1 |

As apparent from the above results, dose-dependent inhibitory effects were observed.

EXAMPLE 7

Antiangiogenic Effects (Ex Vivo)

In the same manner as in Example 6, the ex vivo effects of DS4152 were examined in the presence of a steroid. As the steroid, cordisone acetate was used at a dose of 5 mg/kg. 300 mg/kg of DS4152 was administered subcutaneously or orally. DF4152 and H Fraction were also used. The data represents inhibition percentage of CAM vascularization of each group to that of control group with a blood sample collected from the mice administered with saline.

TABLE 10

| Administration route | DS4152 | DF4639 | H Fraction |
|---|---|---|---|
| Subcutaneous | 92.2% | 83.3% | 86.8% |
| Oral | 92.7% | 88.8% | 82.8% |

DS4152 and DF4639 were found to inhibit the CAM angiogenesis by either oral or subcutaneous administration.

EXAMPLE 8

Antiangiogenic Effects (Ex Vivo)

Male ICR mice were orally administered with a solution of DS4152 dissolved in physiological saline. A saline suspension of a steroid was administered orally or intramuscularly, either in combination with DS4152 or alone. Blood samples collected after 6 hours were prevented from coagulation with a 0.313% aqueous solution of sodium citrate. Each blood sample was added to the 5 day CAM in the same manner as in the direct method. The inhibitory effects were judged after two days. Results were expressed by inhibition ratios (%) of CAM vascularization of each group to that of control group with a blood sample collected from the mice with saline. (Table 11).

TABLE 11

| Steroid | | Dose (mg/kg) | Dose of DS4152 (mg/kg; p.o.) | Inhibition rate of angiogenesis (%) |
|---|---|---|---|---|
| Agent | Route | | | |
| Cortisone acetate | p.o. | 5 | 0 | 7.7 |
|  |  |  | 30 | 75.1 |
| Tetrahydro S | p.o. | 1 | 0 | −2.6 |
|  |  |  | 30 | 71.7 |
|  |  | 5 | 0 | −17.3 |
|  |  |  | 30 | 80.7 |
| Epithiostanol | i.m. | 5 | 0 | 4.0 |
|  |  |  | 30 | 5.2 |
|  |  | 50 | 0 | 13.4 |
|  |  |  | 30 | 23.4 |
|  |  | 100 | 0 | 24.2 |
|  |  |  | 30 | 37.6 |

EXAMPLE 9

Antiangiogenic Effects (Ex Vivo)

In the same manner as in Example 8, antiangiogenic effects of tamoxifen were examined with or without DS4152.

TABLE 12

| Dose (mg/kg) | | Inhibition rate of angiogenesis (%) |
|---|---|---|
| Tamoxifen citrate (subcutaneous) | DS4152 (administration route) | |
| 100 | 0 | −6.1 |
| 100 | 30 (subcutaneous) | 61.2 |
| 100 | 0 | −11.0 |
| 100 | 30 (oral) | 40.0 |

As apparent from Table 12, no influence was given to the vascularization of CAM with the blood sample from mice only with tamoxifen citrate. However the sample collected from the mouse with the combination of tamoxifen and subcutaneous or oral DS4152 (30 mg/kg) inhibited markedly the CAM vascularization. Subcutaneous administration of DS4152 showed greater synergistic effect.

EXAMPLE 10

Antitumor Test

Male C57BL/6 mice were each inoculated subcutaneously with $1 \times 10^6$ cells of ovarian ascites tumor M5076 derived from syngeneic mice. Five days after the inoculation, DS4152 was subcutaneously administered at a daily dose of 30 mg/kg 6 times a week. Remarkable anti-tumor effects and a significant extension of survival days were recognized. As shown in Table 13, the mean tumor weight on the 21st day after the inoculation was 37% of the control (63% inhibition) and the median survival day was increased as many as 33% over the control.

The mean tumor weight was determined in the following manner. Namely, the lengths of both major and minor axes of a tumor mass were measured and then mean tumor weight was calculated in accordance with the following formula.

Mean tumor weight = (major axis) x (minor axis)$^2 \times \frac{1}{2}$

TABLE 13

| Group | Control group | DS4152-administered group |
|---|---|---|
| Tumor line | M5076 | M5076 |
| Dose (mg/kg) | 0 | 30 |
| Tumor weight, in mg[a] | 2.39 ± 0.18 | 0.89 ± 0.09 |
| (T/C, %) | (100) | (37) |
| Increased life[b] span (ILS, %) | 0 | 33 |

[a]Mean tumor weight on the 21st day after inoculation ± standard error. The data in parentheses indicate the percentages of the respective mean weights.
[b](The median survival days of the drug—administered group/those of the control - 1 × 100.

EXAMPLE 11

Antitumor Test

Male ICR mice (5 weeks old) were each inoculated subcutaneously with 1×10$^6$ cells of Sarcoma 180 (S180). From the 3rd day, a saline suspension of cortisone acetate was administered at a dose of 250 mg/kg/day for 3 days and then at a dose of 100 mg/kg/day for 1 day.

DS4152 was dissolved in physiological saline and administered at a dose of 0.61 or 6.1 mg/mouse subcutaneously or orally once a day for 4 days. On the 7th day after the inoculation, the mice were sacrificed to compare their tumor weights with those of the control mice.

TABLE 14

| | Tumor weight | |
|---|---|---|
| Treatment | Mean weight ± standard error | TC, % |
| Physiological saline (p.o.) | 0.361 ± 0.191 | 100.0 |
| Physiological saline (s.c.) | 0.391 ± 0.122 | 100.0 |
| Cortisone acetate | 0.340 ± 0.162 | 94.2 |
| DS4152 (0.61 mg/mouse, p.o.) | 0.361 ± 0.070 | 100.0 |
| DS4152 (6.1 mg/mouse, p.o.) | 0.261 ± 0.077 | 72.3 |
| DS4152 (0.61 mg/mouse, p.o.) + cortisone acetate | 0.063 ± 0.018 | 17.5* |
| DS4152 (6.1 mg/mouse, p.o.) + cortisone acetate | 0.028 ± 0.011 | 7.4* |
| DS4152 (0.61 mg/mouse, s.c.) | 0.322 ± 0.071 | 82.4 |
| DS4152 (6.1 mg/mouse, s.c.) | 0.355 ± 0.115 | 90.8 |
| DS4152 (0.61 mg/mouse, s.c.) + cortisone acetate | 0.063 ± 0.036 | 16.1** |
| DS4152 (6.1 mg/mouse, s.c.) + cortisone acetate | 0.035 ± 0.015 | 6.9** |

*P < 0.05, **P < 0.01, by the Student's t-test.

EXAMPLE 12

Antitumor Test

C3H/He male mice (5 weeks old) were each inoculated subcutaneously with 4×10$^6$ cells of mouse mammary carcinoma MM46. Mice were randomized after measuring the diameters of the resultant tumors on the 7th day. In addition, male ICR mice (5 weeks old) were each inoculated subcutaneously with 1×10$^6$ cells of Sarcoma 180 (S180). On the 3rd days, the mice were randomized. A saline suspension of tamoxifen citrate was administered once a day for 4 days to the MM46-bearing mice on the 7th day after inoculation and to the S180-bearing mice on the 3rd day after inoculation. DS4152 and heparins were individually dissolved in physiological saline and administered either orally or subcutaneously once a day for 4 days at a dose of 30 mg/kg/day or 300 mg/kg/day. On the 5th day after the beginning of the administration, the animals were sacrificed. The tumor weights were compared with those of the control mice administered only with physiological saline (Table 15).

TABLE 15

| Tumor line | Sulfated polysaccharide | | | Subcutaneous dose of tamoxifen citrate (mg/kg) | Tumor weight | |
|---|---|---|---|---|---|---|
| | Agent | Dose (mg/kg) | Route | | Mean ± S.D. (mg) | (T/C %) |
| MM46[1] | — | — | — | 0 | 482 ± 85 | (100) |
| | — | — | — | 100 | 273 ± 27* | (6.6) |
| | DS-4152 | 30 | Subcutaneous | 100 | 85 ± 22*** | (17.6) |
| | DS-4152 | 30 | Oral | 100 | 141 ± 34*** | (29.3) |
| S180[2] | — | — | — | 0 | 307 ± 29 | (100) |
| | — | — | — | 100 | 298 ± 31 | (97) |
| | DS-4152 | 30 | Subcutaneous | 100 | 131 ± 31** | (45) |
| | DS-4152 | 30 | Oral | 100 | 151 ± 6** | (49) |
| | Low molecular weight heparin | 300 | Oral | 100 | 202 ± 22* | (66) |
| | Heparin | 300 | Oral | 100 | 203 ± 13* | (66) |

[1]Mammary carcinoma,
[2]Sarcoma.
*Significant difference from the control, p < 0.05.
**Significant difference from the control, p < 0.01.

As shown in Table 14, the tumor weights of the mice in the group administered only with cortisone acetate were not different from those of the mice in the group administered with physiological saline. Remarkable growth inhibitory effects were obtained in the presence of DS4152, and the tumor weights of the mice were 6.9–17.5% of the tumor weights of the control mice.

As shown in Table 15, the growth of the mammary carcinoma MM46 was inhibited by the single administration of tamoxifen citrate although the degree of the inhibition rate was not so high. However, tamoxifen citrate did not affect the growth of the sarcoma S180 when administered alone. When tamoxifen citrate was used in combination with DS4152 or heparin, the inhibitory effects against the growth of the MM46, which is sensitive to tamoxifen citrate, was markedly enhanced and significant inhibitory effects were also achieved against the sarcoma S180 which is insensitive to tamoxifen citrate. Among the drugs employed in combination with tamoxifen citrate, DS4152 exhibited best results although its dose was as little as one tenths the other drugs.

EXAMPLE 13

Granule

In a manner known commonly in the art, 500 mg of a granular preparation were obtained from 6 mg of DS4152, 300 mg of lactose, 144 mg of corn starch, 30 mg of calcium carboxymethylcellulose and 20 mg of hydroxypropylcellulose. This granular preparation may be administered at a daily dose of 500 mg–5 g, which depends on the symptom of each patient.

EXAMPLE 14

Injection

In injection-grade distilled water, 12 mg of DS4152 and 90 mg of sodium chloride were dissolved to a total volume of 10 ml. After filtration of the resultant solution through a membrane filter, the filtrate was filled in an ampoule, followed by sterilization at 115° C. for 30 minutes to provide an injection.

EXAMPLE 15

Tablet

A tablet was prepared by, mixing and tabletting, in a manner known commonly in the art, 6 mg of DS4152, 20 mg of tamoxifen citrate, 50 mg of lactose, 15.5 mg of corn starch, 5 mg of calcium carboxymethylcellulose, 3 mg of hydroxypropylcellulose and 0.5 mg of magnesium stearate.

Having now fully described the invention, it will be apparent to one of ordinary skill in the art that many changes and modifications can be made thereto without departing from the spirit or scope of the invention as set forth herein.

We claim:

1. A sulfated polysaccharide DS4152 having, as the sodium salt thereof, the following physicochemical characteristics:

(1) Molecular weight (by the gel filtration method): 29,000±3,000

(2) Elemental analysis:
C:24.42–25.76%
H:3.34–3.98%
N:0.51–0.89%
S:10.6–11.7%
P:0.77–1.06%

(3) Sugar and protein contents:
Sugar content(%): 57±3 (by phenolsulfuric acid method; standard: galactose)
Protein content (%): 1±0.5 (by the Lowry-Folin's method; standard: bovine serum albumin)

(4) Specific rotatory power:
$[\alpha]_D^{25}$: −37°±1° (0.5% aq. solution)

(5) Characteristic absorption bands in infrared absorption spectrum:
1240, 840 (shoulder), 810 (cm$^{-1}$; KBr)

(6) Solubility:
Freely soluble in water but practically insoluble in organic solvents.

(7) Color reaction:
Positive in the phenol-sulfuric acid reaction, anthrone-sulfuric acid reaction, biuret reaction and Lowry-Folin's reaction, in the form of an acid hydrolyzate, also positive in the Elson-Morgan's reaction and ninhydrin reaction, negative in the carbazole reaction and Sakaguchi reaction.

(8) Distinction of acidic, neutral or basic:
pH 6–8 (3% aq. solution)

(9) Contents of constituent sugar, sulfate groups and phosphorus:
molar ratio of D-glucose: D-galactose:SO$_3$Na:P(-phosphorus) approximately 10:61:73:6.

(10) Constituent amino acids and amino sugars:
analysis of an acid hydrolysate by an amino acid analyzer indicates the existence of alanine, glycine, glutamic acid, diaminopimelic acid, glucosamine and muramic acid.

2. An angiogenesis inhibitor comprising an effective amount of a sulfated polysaccharide DS4152 as the active ingredient and a medicinally-acceptable carrier or excipient.

3. The angiogenesis inhibitor as claimed in claim 2, wherein said inhibitor is effective for rheumatoid arthritis, proliferating retinitis, psoriasis, diabetic retinitis and retrolental fibroplasia.

4. An antitumor agent comprising a sulfated polysaccharide DS4152 as the active ingredient and a medicinally-acceptable carrier or excipient.

5. An angiogenesis inhibitor comprising, as active ingredients, a sulfated polysaccharide DS4152 and a steroid or antiestrogen.

6. The angiogenesis inhibitor as claimed in claim 5, wherein the steroid is selected from a glucocorticoid, androgen or follicle hormone.

7. The angiogenesis inhibitor as claimed in claim 5, wherein the antiestrogen is selected from clomiphene, nafoxidine, tamoxifen, 4-hydroxytamoxifen and N-desmethyltamoxifen and physiologically-acceptable salts thereof.

8. The angiogenesis inhibitor as claimed in claim 5, wherein said inhibitor is effective for rheumatoid arthritis, proliferating retinitis, psoriasis, diabetic retinitis and retrolental fibroplasia.

9. An antitumor agent comprising, as active ingredients, a sulfated polysaccharide DS4152 and a steroid or antiestrogen.

10. A method for inhibiting angiogenesis, which comprises administering to a subject an effective amount of sulfated polysaccharide DS4152.

11. The method according to claim 10, wherein rheumatoid arthritis, proliferating retinitis, psoriasis, diabetic retinitis, retrolental fibroplasia or tumor growth is inhibited by said sulfated polysaccharide DS4152.

12. The method according to claims 10 or 11, wherein said sulfated polysaccharide DS4152 is administered together with a steroid or antiestrogen.

13. The method according to claim 12, wherein said steroid is a glucocorticoid, androgen or follicle hormone.

14. The method according to claim 12, wherein said antiestrogen is clomiphene, nafoxidine, tamoxifen, 4-hydroxytamoxifen, N-desmethyltamoxifen or physiologically-acceptable salts thereof.

* * * * *